(12) United States Patent
Gold

(10) Patent No.: US 7,449,571 B2
(45) Date of Patent: Nov. 11, 2008

(54) HALOGENATED AMINOQUINOLINES AND OLIGONUCLEOTIDES CONTAINING THE SAME

(75) Inventor: Barry I. Gold, Pittsburgh, PA (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 267 days.

(21) Appl. No.: 11/152,510

(22) Filed: Jun. 14, 2005

(65) Prior Publication Data

US 2006/0281907 A1 Dec. 14, 2006

(51) Int. Cl.
*A61K 31/7032* (2006.01)
*A61K 31/4704* (2006.01)
*C07H 7/06* (2006.01)
*C07D 215/38* (2006.01)

(52) U.S. Cl. ............... 536/29.2; 514/23; 514/313; 546/22; 546/159

(58) Field of Classification Search .................. None
See application file for complete search history.

(56) References Cited

U.S. PATENT DOCUMENTS 5,844,110 A 12/1998 Gold

OTHER PUBLICATIONS

Li, J-S, et al., "Synthesis of C-Nucleotides Designed to Participate in Triplex Formation with Native DNA: Specific Recognition . . .," J.Org. Chem., 70:8764-8771, (2005).

*Primary Examiner*—Shaojia Anna Jiang
*Assistant Examiner*—Eric S Oslon
(74) *Attorney, Agent, or Firm*—Patrick J. Hagan, Esq.; Dann, Dorfman, Herrell and Skillman, P.C.

(57) ABSTRACT

Novel synthetic monomers that have the capacity to be assembled into defined oligomers which bind with sequence specificity to duplex Watson-Crick DNA via a triple helix motif are provided.

16 Claims, 6 Drawing Sheets

| OL | potential triplex structure | pH | $T_M$ 260 nm | $T_M$ 325 nm |
|---|---|---|---|---|
| OL-1 | $C_5$ — T-T-T-T-T-T-5'<br>3'-W W W W W W<br>A-A-A-A-A-A — $C_5$ | 6<br>7<br>8 | 38.1<br>37.9<br>41.8 | n.d.<br>38.8<br>40.1 |
| OL-2 | $C_5$ — A-A-A-A-A-A<br>W W W W W W-5' $C_5$<br>3'-T-T-T-T-T-T | 6<br>7<br>8 | 38.4<br>37.6<br>40.6 | n.d.<br>40.4<br>46.1 |
| OL-3 | $C_5$ — A-A-A-G-A-A<br>W W W W W W-5' $C_5$<br>3'-T-T-T-C-T-T | 6<br>7<br>8 | 38.1<br>37.9<br>41.8 | n.d.<br>n.d.<br>n.d. |
| OL-4 | $C_5$ — A-A-A-T-A-A<br>W W W W W W-5' $C_5$<br>3'-T-T-T-A-T-T | 6<br>7<br>8 | 38.1<br>37.9<br>41.8 | n.d.<br>n.d.<br>n.d. |
| OL-5 | $C_5$ — G-G-G-G-G-G<br>$W^+W^+W^+W^+W^+W^+$-5' $C_5$<br>3'-C-C-C-C-C-C | 6<br>7<br>8 | 38.4<br>37.6<br>40.6 | n.d.<br>40.4<br>46.1 |

HALOGENATED AMINOQUINOLINES AND OLIGONUCLEOTIDES CONTAINING THE SAME

Pursuant to 35 U.S.C. Section 202(c), it is acknowledged that the United States Government has certain rights in the invention described herein, which was made in part with funds from the National Institutes of Health Grant No. RO1 GM068430.

FIELD OF THE INVENTION

The present invention relates to the synthesis of novel monomers and to the monomers per se, which are capable of assembly into defined oligomers that bind with sequence specificity to duplex Watson-Crick DNA via a triple helix motif. The novel monomer molecules of the present invention, when assembled into defined oligomeric sequences, may be used for a variety of purposes related to target-specific control of gene expression.

BACKGROUND OF THE INVENTION

Triple helix ("triplex") structures were first reported in 1957 from the combination of poly-adenylic acid ("poly-A") with two equivalents of poly-uridylic acid ("poly-U") (Felsenfeld et al., J. Amer. Chem. Soc. 79: 2023, 1957). It is known that the third pyrimidine strand, which resides in the wider major groove of duplex DNA, recognizes homopurine stretches and binds parallel to the purine strand (referred to as "parallel motif" or "pyrimidine motif"). In another approach, which uses purines in the third strand, the recognition of the purine stretch in the duplex is anti-parallel (referred to as "purine motif" or "anti-parallel motif").

The general requirement for homogeneous runs of purine/ pyrimidine nucleotide bases in the formation of a traditional triple helix structure has resulted from the need to use natural nucleotide bases in the complementary third strand, due to the unavailability of any other molecules to substitute effectively for these natural bases. Traditional third strand binding has therefore been restricted to homogeneous runs of natural purines or pyrimidines because of spacial restrictions associated with Hoogsteen base pairing of the $N^7$— and $X^6$—positions of naturally occurring purines (X is the $NH_2$ or oxygen for adenine and guanine, respectively) in the homopurine strand of the Watson-Crick duplex DNA. Because only the homopurine strand of the duplex provides hydrogen bonding information in such a structure, the third strand binds asymmetrically in the major groove nearest to the sugar-phosphate backbone of the purine strand. As a result, any deviation from homopurine sequence requires that the traditional third strand actually cross over to the other side of the major groove. Limitations in the span and flexibility of the 5'-3'-linked deoxyribose/phosphodiester backbone do not allow this to occur. Thus, any pyrimidine interruption in the homopurine strand cannot be accommodated by the traditional third strand and also significantly destabilizes traditional triple helix formation. In addition to the crossover barrier, the major groove hydrogen-bonding information on the purine molecule targeted by the third strand is not the same for A—T as compared to T—A pairing.

There is intense interest in the design of molecules that can bind sequence specifically via a triple helix motif to mixed purine/pyrimidine sequences in native Watson-Crick DNA (Griffin and Dervan (1989) Science, 245:967-970; Horne and Dervan (1990) J. Am. Chem. Soc., 112:2435-2437; Jayasena and Johnston (1992) Nucl. Acids Res., 20:5279-5288; Gowers and Fox (1999) Nucl. Acids Res., 27:1569-1577; Buchini et al. (2004) J. Angew. Chem. Int. Ed., 43:3925-3928; Craynest et al. (2004) Tetrahedron Lett., 45:6243-6247). To achieve this goal, a set of four C-glycoside bases (Li et al. (2003) J. Am. Chem. Soc., 125:2084-2093), i.e., 2-amino-4-(2'-deoxy-β-D-ribofuranosyl) quinoline (antiGC), 2-amino-5-(2'-deoxy-β-D-ribofuranosyl)quinoline (antiCG), 2-amino-4-(2'-deoxy-β-D-ribofuranosyl)quinazoline (antiAT), and 2-amino-5-(2'-deoxy-β-D-ribofuranosyl) quinazoline (antiTA), which differentiate between the four base paring schemes in the major groove, i.e., G:C, C:G, A:T, T:A, respectively, have been previously generated by the present inventor.

In stark contrast to the traditional triple helix motifs which require homogenous stretches of either purine or pyrimidine nucleotide bases as targets for binding, the above synthetic bases and nucleotides permit any known duplex DNA and/or RNA sequences to be targeted, including the usual duplex DNA and/or RNA sequences which contain heterogeneous (mixed) sequences of purines and pyrimidines. Synthetic oligomers containing these bases recognize major-groove hydrogen bonding information associated with the purine and, optionally, the pyrimidine bases contained in each interstrand nucleotide base-pair combination in the targeted gene sequence. The orientation of the synthetic oligonucleotide relative to the duplex may be arbitrarily defined as running antiparallel to the left strand in the major groove that runs 5' to 3' top to bottom. Oligomers comprising the synthetic monomeric compounds described above can form stable sequence-specific triple helix structures with duplex (doublestranded) Watson-Crick DNA molecules, and do so in such a way that the sugar-phosphate backbone of the synthetic oligomer lies near the center of the major groove of the duplex DNA structure. Because these oligomers recognize nucleotide base sequences in double-stranded DNA without the limitation that the binding be done at low pH, or that the targeted sequence be only a homogeneous sequence of either purines or pyrimidines, the construction of triple helix-forming oligomers directed against any known heterogeneous sequence of purines and pyrimidines (as is commonly found in viral or non-viral sequences) is straightforward.

U.S. Pat. No. 5,844,110, which is currently owned by the present applicants, discloses novel monomeric compositions which are substituted quinoline- or quinazoline-based structures capable of hydrogen bonding specifically with interstrand purine-pyrimidine base pairs in a double-stranded Watson-Crick DNA molecule. The monomeric compounds of the '110 patent are capable of being assembled in specific sequences into oligomers capable of binding with sequence specificity to duplex DNA via a triple helix motif.

Of the four C-glycoside bases described and claimed in the '110 patent, antiTA (Li et al. (2003) J. Am. Chem. Soc., 125:2084-2093), antiGC (Li et al. (2004) Biochemistry, 43:1440-1448), and antiCG (Li et al. (2005) submitted J. Am. Chem. Soc.) have been synthesized by the coupling of a protected ribofuranoid glycal with a halogenated heterocycle using a Pd-mediated Heck-type reaction (Cheng et al. (1985) J. Org. Chem., 50:2778-2780; Davies, G. D. (1992) J. Org. Chem., 57:4690-4696; Farr et al. (1992) J. Org. Chem., 57:2093-2100; Farr et al. (1990) Carbohydr. Chem., 9:653-660). Notably, the synthesis of oligomers with antiAT by solid phase synthesis has proven to be less than ideal because of partial decomposition of antiAT during deprotection unless prolonged deprotection times at lower temperatures were employed.

SUMMARY OF THE INVENTION

The present invention broadly relates to halogenated amionoquinolines and the formation of triplexes of DNA using the same.

According to one aspect of the invention, there is provided a compound of the formula:

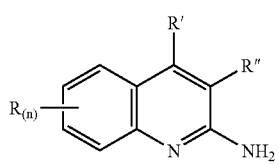
(I)

wherein R is an electron withdrawing group selected from the group consisting of halo, nitro, carboxy, cyano, aryl, said aryl substituent being optionally substituted, heteroaryl, said heteroaryl substituent bring optionally substituted, —OC(A)$_3$, —C(A)$_3$, —C(A)$_2$—O—C(A')$_3$, —(CO)-Q, —SO$_2$—C(A)$_3$, —SO$_2$-aryl, —C(NQ)Q, —CH═C(Q)$_2$, —C≡C-Q, in which each A and A' is independently H, halo, —CN, —NO$_2$, —OH, or C$_{1-4}$ alkyl optionally substituted with 1-3 halo, —OH, NO$_2$, and Q is selected from the group consisting of H, —OH, alkyl optionally substituted with 1-3 halo, —OH, —O-alkyl, and —O-cycloalkyl, n is an integer from 1-4, each said R substituent being the same or different when the benzene ring of the compound of Formula (I) is polysubstituted; R' is a selected from the group consisting of ribose and deoxyribose, optionally comprising at least one phosphate (e.g., one phosphate at the 5' position), the phosphoramidite form of such compound, and a unit of an oligonucleotide analog backbone; and R" is H or R. In another embodiment R is selected from the group consisting of fluorine, chlorine, nitro, and cyano. In another embodiment R" is selected from the group consisting of hydrogen, fluorine, chlorine, nitro, and cyano. In another embodiment, R" is hydrogen.

Preferred among the compounds of the invention are those having the formula:

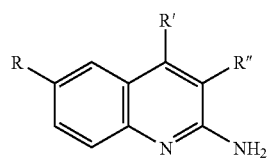
(II)

wherein R is selected from the group consisting of halo, nitro, carboxy, cyano, aryl, said aryl substituent being optionally substituted, heteroaryl, said heteroaryl substituent bring optionally substituted, —OC(A)$_3$, —C(A)$_3$, —C(A)$_2$—O—C(A')$_3$, (CO)-Q, —SO$_2$—C(A)$_3$, —SO$_2$-aryl, —C(NQ)Q, —CH═C(Q)$_2$, —C≡C-Q, in which each A and A' is independently H, halo, —CN, —NO$_2$, —OH, or C$_{1-4}$ alkyl optionally substituted with 1-3 halo, —OH, NO$_2$, and Q is selected from the group consisting of H, —OH, alkyl optionally substituted with 1-3 halo, —OH, —O-alkyl, and —O-cycloalkyl, n is an integer from 1-4, each said R substituent being the same or different when the benzene ring of the compound of Formula (I) is polysubstituted; R' is a selected from the group consisting of ribose and deoxyribose, optionally comprising at least one phosphate (e.g., one phosphate at the 5' position), the phosphoramidite form of such compound, and a unit of an oligonucleotide analog backbone; and R" is H or R.

According to another aspect of the invention, methods are provided for the preparation of the compounds of Formula I above. One method comprises providing a precursor compound of the Formula:

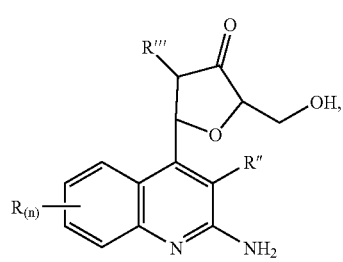
(III)

wherein R''' is H or OH, and reacting the precursor compound with a reducing agent under conditions effective to yield the desired compound.

The precursor compound of Formula III can be prepared by reacting a compound of the formula

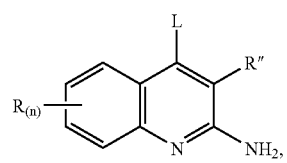
(IV)

wherein L represents a leaving group, with an optionally protected form of 1,4-anhydro-2-deoxy-D-erythro-pent-1-enitol, in the presence of a catalyst for a Hecht reaction such as tris(dibenzylideneacetone)dipalladium to yield the precursor compound. The compound of Formula IV can be obtained by reacting a compound of the formula

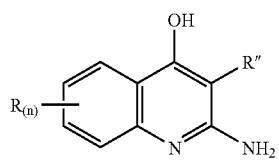
(V)

with a reagent that is effective to replace the hydroxyl substituent of the compound of Formula (V) with the leaving group (L).

BRIEF DESCRIPTIONS OF THE DRAWING

FIG. 3 is a table showing the sequences of oligomers (OL's 1-5), the potential triplex structures (solid vertical bonds indicate two Hoogsteen H-bonds can be formed; horizontal open bonds indicate a mismatch) and $T_M$'s in 10 mM sodium phosphate buffer containing 200 mM NaCl as a function of pH.

Figure 4:
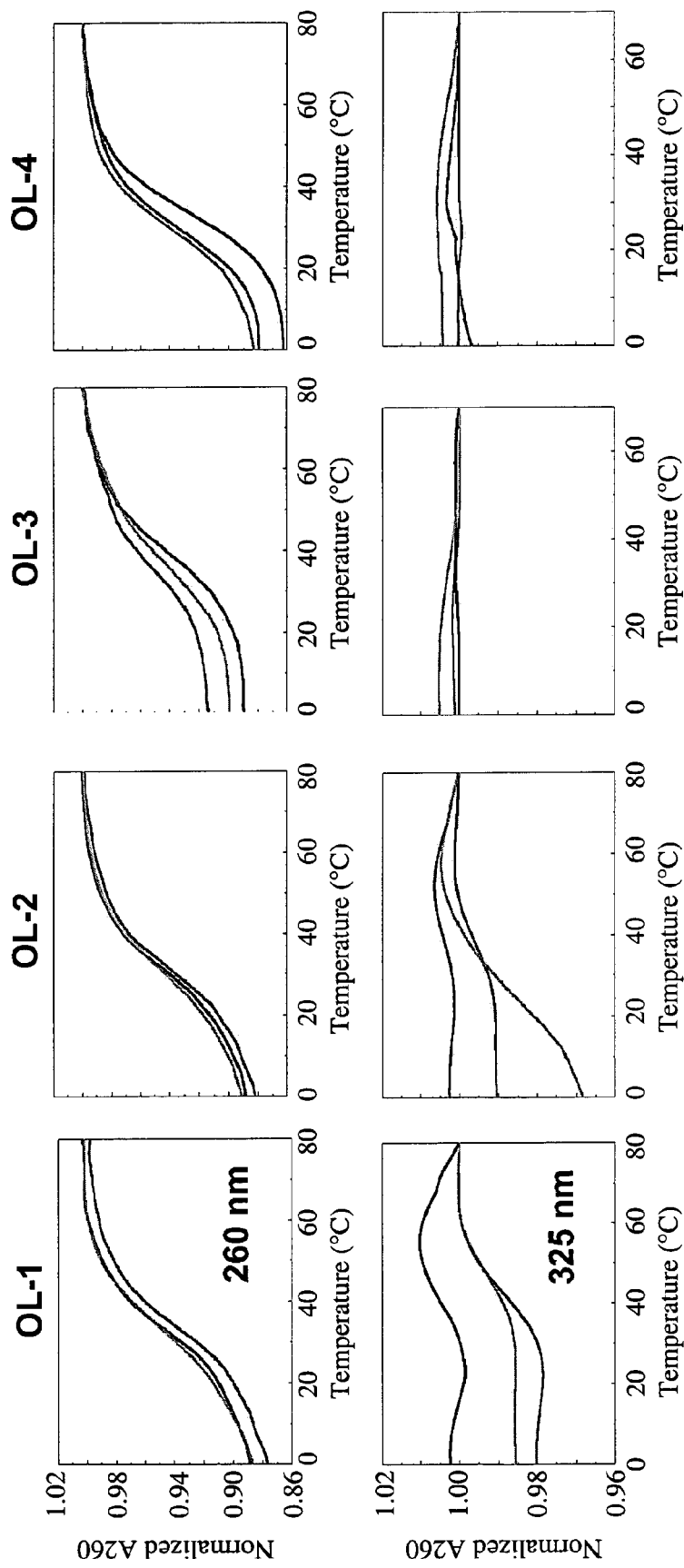

FIG. 4 shows graphical representations of $T_M$ curves at 260 (top row) and 325 nm (bottom row) in 10 mM sodium phosphate buffer containing 200 mM NaCl at pH 6.0 (dark line), 7.0 (medium line), and 8.0 (light line) for oligonucleotides OL-1, OL-2, OL-3 with a G:C mismatch; and OL-4 with a T:A mismatch.

Figure 5:
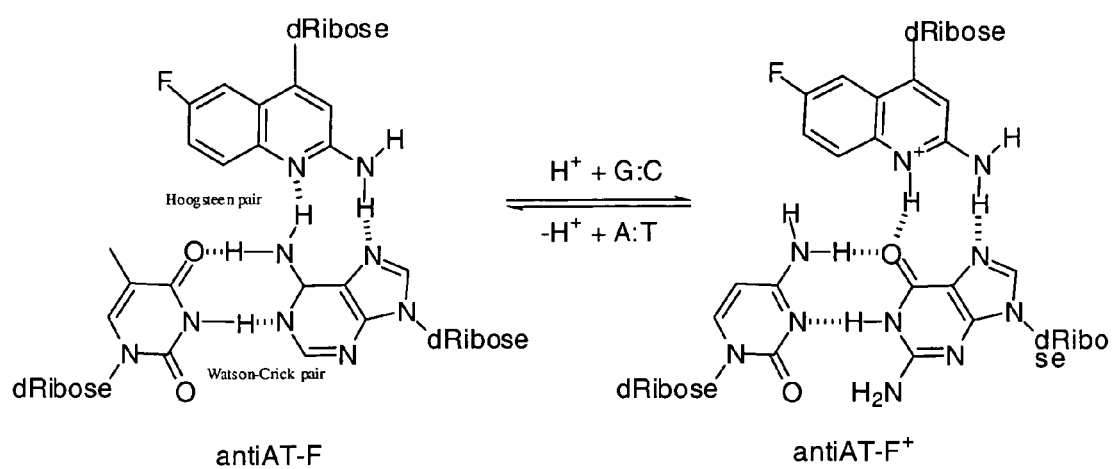

FIG. 5 is schematic demonstrating the effect of pH on Hoogsteen binding of antiAT-F to A:T or antiAT-F+ to G:C Watson-Crick pair.

DETAILED DESCRIPTION OF THE INVENTION

Figure 1A:
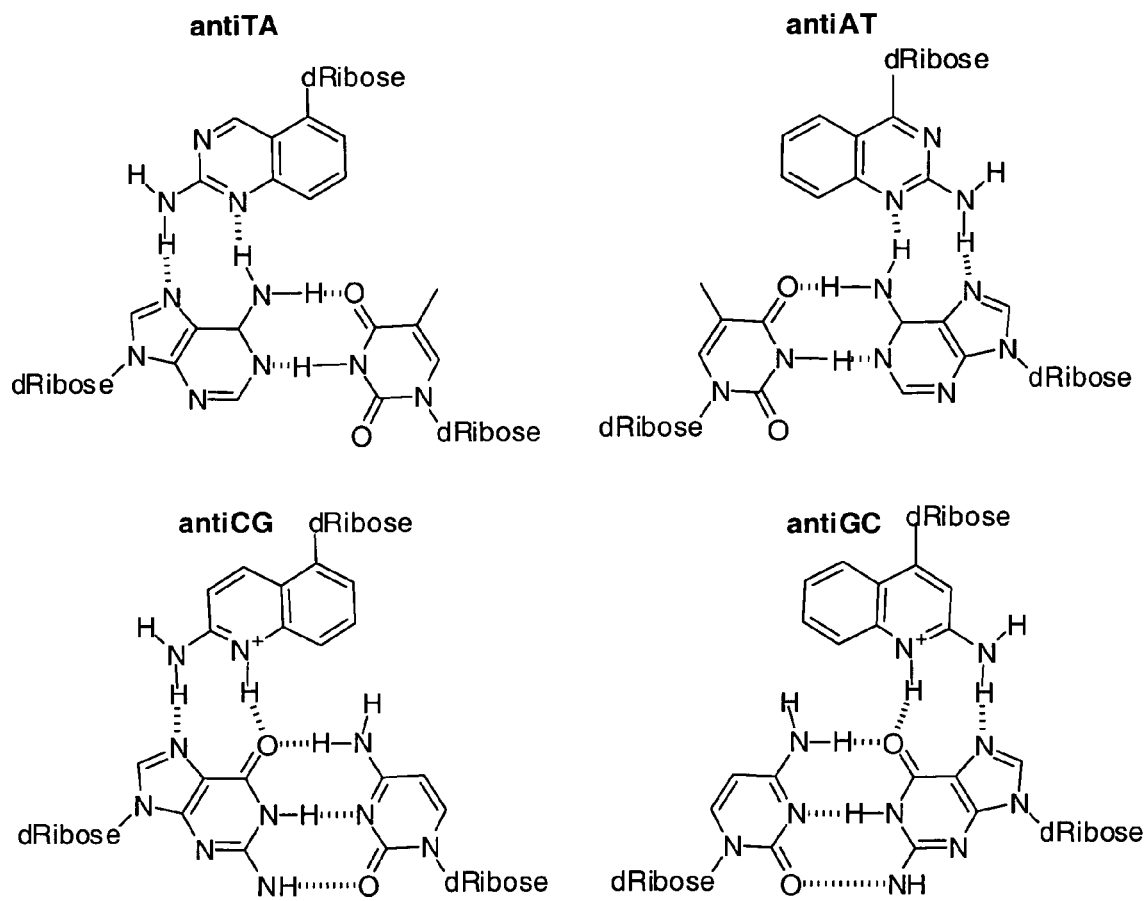
FIG. 1A shows the structures of synthetic monomers (antiAT, antiTA, antiCG, and antiGC) and their duplex Watson-Crick partners.
Figure 1B:
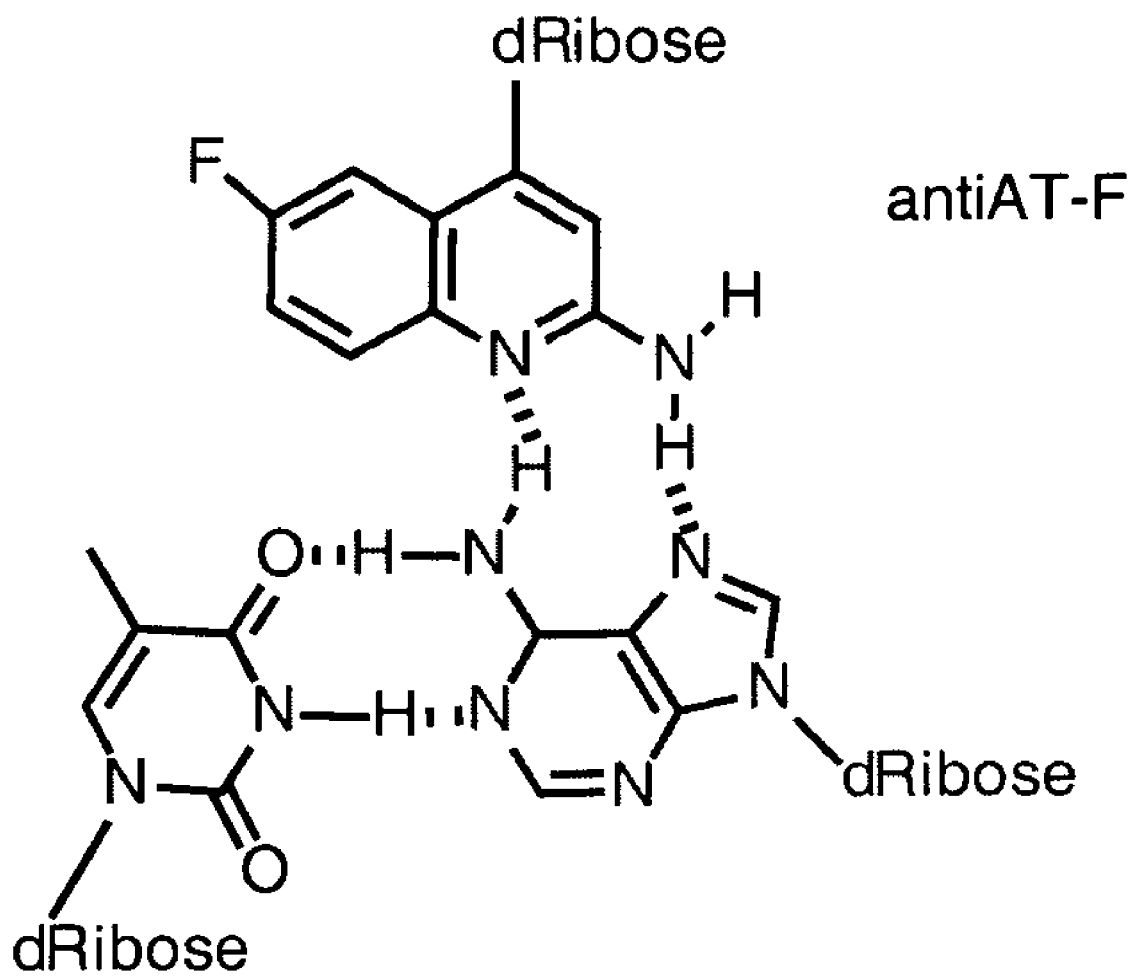
FIG. 1B shows the structure of antiAT-F.

As stated hereinabove, the present inventor previously synthesized modified bases which allow for the formation of triplex DNA by the binding of the major grove of duplex DNA. Such modified bases and nucleotides and oligonucleotides comprising the same are the subject of U.S. Pat. No. 5,844,110, the entire disclosure of which is incorporated by reference herein. Four of these synthetic bases (AntiTA, AntiAT, AntiGC, and AntiCG) are depicted in FIG. 1A. In accordance with the instant invention, novel synthetic bases are provided, namely compounds having formula I above. Superior results have been obtained using antiAT-F (2-amino-6-fluoroquinolin-4-yl C-deoxynucleoside) in comparison to antiAT in solid phase oligonucleotide synthesis, antiAT-F being a preferred embodiment of the instant invention.

The key difference between the antiAT aminoquinazoline and the antiGC aminoquinoline is that the former is less basic (pKa, 4.8 vs 7.2, respectively) (Li et al.(2003) J. Am. Chem. Soc., 125:2084-2093; Li et al. (2004) Biochemistry 2004, 43:1440-1448). Therefore, antiAT is not protonated at physiological pH and can form the two required H-bonds with an A:T base pair via its H-bond acceptor and H-donator atoms (FIG. 1A). In contrast, antiGC is protonated at neutral pH and binds to G:C using its two H-bond donors. A fluoro derivative would theoretically reduce the pKa of the 2-aminoquinoline system and thus mimic quinazoline. The F group, based upon DNA models, was not anticipated to present any steric barriers to triplex formation.

Figure 2:
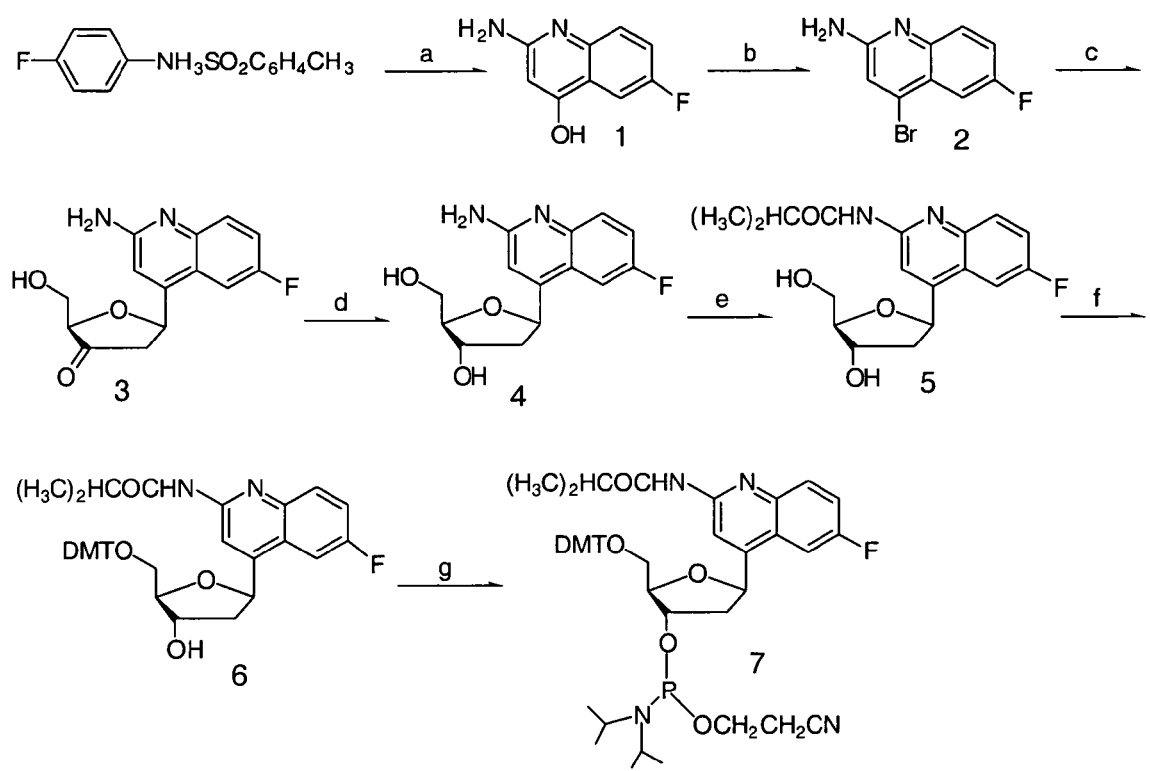
FIG. 2 is a scheme for the synthesis of antiAT-F (4).

A method of synthesis of antiAT-F is shown in FIG. 2. The identified reactions are: (a) NCCH$_2$CO$_2$Et, 210-260° C., 1.25 hours (15% yield); (b) POBr$_3$/PBr$_3$, 140-160° C. (57% yield); (c) Pd(II)-(dba)$_3$, 1,4-anhydro-2-deoxy-D-erthropent-1-enitol, dioxane, reflux, 12 hours/TBAF, AcOH, 0° C., 5 min (33% yield); (d) NaBH(OAc)$_3$, −22° C., 1 hour (70% yield); (e) (i-PrCO)$_2$O, pyridine, room temperature, 2 hours (47% yield); (f) DMTrCl, pyridine, Et$_3$N, DMAP, room temperature, 72 hours, 58% yield; and (g) 2-cyanoethyl-N,N'-diisopropylchlorophosphoramidite, N,N-diisopropylethylamine, CH$_2$Cl$_2$, room temperature, 1 hour, 84% yield.

The formation of the 2-amino-6-fluoroquinoline (1) ring system was accomplished by the fusion of 4-fluoroaniline salt with ethyl cyanoacetate. The hydroxy group of 1 was converted into the 4-bromo compound that was needed in the subsequent Heck coupling. The coupling of 2 with the ribofuranoid glycal has been used previously by others as a route to C-glycosides (Cheng et al. (1985) J. Org. Chem., 50:2778-2780; Davies, G. D. (1992) J. Org. Chem., 57:4690-4696; Farr et al. (1992) J. Org. Chem., 57:2093-2100; Farr et al. (1990) Carbohydr. Chem., 9:653-660) and to prepare antiTA (Li et al.(2003) J. Am. Chem. Soc., 125:2084-2093), antiGC (Li et al.(2004) Biochemistry, 43:1440-1448), and antiCG nucleotides. Stereoselective reduction of the ketone to the alcohol gives the desired deoxynucleoside 4. The pKa of antiAT-F was calculated as 6.7 using either UV-vis or fluoresence vs pH experiments. In addition to the change in the extinction coefficient upon protonation, there is a small blue shift for the $\lambda_{max}$.

Incorporation of the antiTA-F phosphoramidite (7) into oligomers followed standard procedures and gave >98% coupling yields. After deprotection, HPLC purification and desalting, the purity and structure of the oligomers were confirmed by analytical HPLC and MALDI-TOF MS.

Synthetic oligonucleotides of the invention comprise one or more compounds of Formula I. In a particular embodiment, the synthetic oligonucleotide comprises at least one antiAT-F synthetic monomer (nucleotide). The synthetic oligonucleotides of the invention may also comprise other compounds which promote triplex formation, such as antiGC and antiCG. Additionally, the synthetic oligonucleotides may also be tagged with a detectable label (e.g., radioisotope, fluorescent compound); comprise "natural" nucleotides (e.g., adenine, guanine, cytosine, thymine, and uracil); and/or comprise ribose instead of deoxyribose.

The interstrand A—T and T—A base pairings, at the simplest level, are equivalent in terms of hydrogen bonding information. However, there is a subtle difference in the spatial relationship of the three hydrogen bonding atoms (receptor atoms of N7-adenine and 04-thymine and the donor atom of $N^6H_2$) that can be exploited. Two key points are: 1) the steric interaction between the angular C8-H of the quinazoline ring system and the exocyclic NH$_2$ group of adenine; and 2) the requirement that the three atoms in a hydrogen bond interaction (X—H—Y) form an angle of 160°-178°. The anti-TA moiety can form three hydrogen bonds only to an interstrand T—A base pair because the C8-H can only accommodate the correct base pair match. In fact, it does not form more than one reasonable hydrogen bond to the interstrand A—T pair. Similarly, the novel anti-AT moiety of the present invention specifically interacts with interstrand A—T only and not with T—A pairing. Neither of these compound have any steric interaction with the 5-methyl group of thymine.

Exemplary synthetic bases can be produced from syntheses compatible with phosphoramidite chemistry. To facilitate implementation of the DNA triplex strategy of the present invention, it is important that the prepared synthetic oligomers recognize and bind to any duplex DNA sequence. Clearly, the wide use of solid support-based DNA synthesis employing mechanized phosphoramidite chemistry makes this method of oligomer production most attractive. In a preferred embodiment, the sugar-phosphate backbone structure of the synthetic oligomers of the present invention can be readily synthesized as either a phosphodiester or a phosphorothioate backbone. Additionally, persons skilled in the art will understand that a variety of other backbone structures known in the art also may be used to produce the synthetic oligonucleotides of the present invention. These backbones linkages include, without limitation, 5'-2' sugar phosphonate linkage and amino acid linkage (e.g., N-(2-aminoethyl)glycine). Amino acid linkage has been used to produce DNA analogs (termed "PNA") that exhibit hybridization characteristics obeying Watson-Crick hydrogen bonding rules (Egholm et al. (1993) Nature, 365:566-568).

Additional stabilization of triple helical structures using an intercalating molecule linked to the end of the third strand has previously been utilized to show in vivo activity against an eight basepair homopurine/homopyrimidine sequence (Birg, et al. (1990) Nucleic Acids Res., 18:2901). Although the length of duplex DNA which can be targeted using the synthetic oligonucleotides of the present invention is longer than eight basepairs in length, and more stable because of up to three hydrogen bonds per base, the preparation of synthetic oligomer containing an intercalator is yet another embodiment of the present invention.

Synthetic oligonucleotides which are complementary to the sense strand of nucleic acids have become widely recognized in recent years for their ability to inhibit the expression of specific genes (see, e.g., Oligodeoxyribonucleotides: Antisense Inhibitors of Gene Expression, (J. S. Cohen, Ed.) CRC Press, Boca Raton; Fla., 1989; Ausubel et al., eds. Current Protocols in Molecular Biology, John Wiley and Sons, Inc., (1998)). "Antisense" oligonucleotides are traditionally single-stranded nucleic acids which, by hybridizing either to the complementary DNA nucleotide sequence in a target gene, or more commonly, to the messenger RNA (mRNA) transcribed from that gene, are able to reduce or abrogate the function of the targeted gene. In a similar manner, synthetic oligonucleotides of the present invention can be designed to be complementary and to bind with a specific information-bearing sequence of paired nucleotide bases in a targeted double-stranded DNA helix. Because these sequence-specific, complementary synthetic oligonucleotides target duplex (double-stranded) DNA rather than cell and tissue proteins, they have the potential to be drugs that are an order or so of magnitude more selective than traditional drugs. The increased specificity should very significantly reduce problems of unwanted side effects.

The current thinking in antisense oligonucleotide therapy is to utilize homologous DNA-based oligonucleotides as therapeutic agents; i.e., as agents whose nucleotide base sequence is complementary to all or part of the nucleotide sequence of a cellular or viral gene believed to be important in causing or regulating a disease process. Similarly, synthetic oligonucleotides of the instant invention, utilizing the synthetic monomers described herein, can be targeted to selected gene sequences for the purpose of controlling the expression of the targeted gene and formation of its product.

The size of the synthetic oligonucleotide, i.e., the number of bases, is an important consideration. In practice, the length (in base numbers) of a traditional therapeutic antisense oligonucleotide ranges from at least about 8 bases to as many as about 100 bases. Especially preferred are oligonucleotides with from about 14 to about 25 bases. The longer the antisense oligonucleotide, the higher is its affinity for a target sequence when it binds with exact complementarily. Similar considerations exist for the use of the synthetic oligonucleotides of the instant invention. Furthermore, the longer the sequence being utilized, the more unique is the targeted sequence. However, these advantages are offset by the fact that longer oligomers are also more difficult and costly to prepare and more difficult to handle.

The region of the target DNA to which the selected synthetic oligonucleotide is designed to hybridize is an important variable that affects the practice of this invention. Several criteria are used herein to select the targeted region. These are: (i) thermal stability of the hybrid complex; (ii) secondary structure in the targeted DNA region; and (iii) the transcriptional activity of the targeted region (i.e., the targeted region must be transcriptionally active so that physical accessibility is guaranteed).

The synthetic oligonucleotides of the present invention are also useful as research tools, i.e., for experimental modification of a target DNA sequence of interest. For example, synthetic oligonucleotides may be used for targeted delivery of DNA alkylating agents for studying the effect of such agents on gene expression.

The impetus for designing targeted equilibrium binding DNA alkylating agents arises from the knowledge that, although the modification of DNA is the initial step in the mechanism of action for many mutagens, carcinogens and antineoplastic agents, there is currently no common theme to the structure of the adducts or the sites of DNA modification. For example, the powerful liver carcinogen, aflatoxin B, appears to selectively form an adduct at 7-G, and this DNA modification is thought to be responsible for its tumorigenicity. However, the same 7-G site is considered to be relatively unimportant in the induction of hepatic tumors by methylating and ethylating agents that react at a variety of positions on the DNA in addition to 7-G. The diversity and variation in product yields makes it difficult to dissect the importance and roles of individual DNA lesions in mutagenicity and/or cytotoxicity.

In order to understand the mechanism(s) of genotoxic carcinogens, and to design more effective DNA damaging anti-cancer agents, it important to differentiate between DNA adducts that are promutagenic and/or cytotoxic, versus innocuous. Accordingly, it is desirable to design alkylating compounds to generate DNA adducts with groove and/or sequence specificity in order to change the "normal" alkylation pattern of the compound, and to determine the effect of this pattern change on the in vivo toxicity, mutagenicity and mutation specificity of the compound on the target DNA. The synthetic oligonucleotides of the present invention are capable of modification to incorporate various alkylating agents, and therefore should be of particular utility in target-specific delivery of these agents to a DNA sequence under investigation. A preferred method for appending an alkylating functionality on to a synthetiuc oligonucleotide is described in U.S. Pat. No. 5,844,110.

In accordance with the present invention, there is also provided a novel and unexpected method for killing or inhibiting the growth of cancer cells which carry certain genes known to be related to the tumorigenesis process. To illustrate, the gene that encodes the cancer-related p53 protein is a gene target of particular interest to research and clinical oncologists, as it is considered to occur more frequently among human cancers than does any other cancer-related gene yet identified. Accordingly, p53 is a preferred target of the novel compositions of this invention. A number of cancers known to carry this gene are, for example, leukemias, lymphomas, myeloma, breast cancer, gastro-intestinal cancers, and small cell carcinoma of the lung.

The method of the present invention for killing or inhibiting the growth of cancer cells involves contacting cancer cells in vivo or in vitro with a cytotoxically-effective amount of at least one appropriate synthetic oligonucleotide of the instant invention, or pharmaceutically-effective analogs thereof. In a preferred embodiment, the at least one synthetic oligonucleotide, or pharmaceutically-effective analogs thereof, have a synthetic monomer sequence complementary to a sequence of interstrand nucleotide base pairs in the DNA of the p53 gene present in the cancer cells.

The term "cytotoxically-effective amount", as used herein, means an administered amount of a therapeutic preparation comprising at least one synthetic oligonucleotide, which is well below the cytotoxic endpoint of the synthetic oligonucleotide preparation, but which is sufficient to kill or inhibit the growth of target tumor cells containing the targeted gene, in preference to other cells which do not contain the targeted gene. Exemplary of such a targeted cancer-related gene is the gene encoding p53.

The present invention also provides novel methods for treating an individual whose cancer cells contain a certain gene (or genes) which are identified as being related to the process of tumor development. Exemplary of such a gene is the gene encoding the cancer-related p53 protein. The methods for treating an individual with cancer involves the use of antisense synthetic oligonucleotide therapies, in which a cytotoxically-effective amount of a preparation containing at least one anti-p53 antisense synthetic oligonucleotide, or one or more pharmaceutically-effective analogs thereof, is administered as specific drug therapy of cancers which carry the p53 gene. In a preferred embodiment of the present invention, the synthetic oligonucleotide preparation is administered systemically to the individual. Thus, there is provided a method for treating an individual having cancer comprising administering to the individual a sufficient amount of a preparation containing at least one oligonucleotide complementary to duplex DNA in a target gene to kill or inhibit the growth of the cancer cells present in the individual.

It is common to provide cancer-bearing individuals with intensive (potentially lethal) radio- and/or chemotherapy to ablate their tumor burden, followed by rescue with an autologous bone marrow transplant. More recently, rescue with an autologous peripheral stem cell transplant has been performed. However, these transplant procedures will have long-term value only when the autologous transplant cell suspensions are completely free of contaminating tumor cells.

Accordingly, in another embodiment of the present invention, autologous bone marrow cells (or peripheral blood-derived stem cells) from an individual with cancer whose cancer cells contain a known oncogene or cancer-related gene (such as p53, for example) are treated ex vivo with specific antisense synthetic oligonucleotides to the cancer-related gene in order to eliminate the cancer cells which may be contained in the bone marrow or stem cell transplant specimen. This is a specific improvement over the current procedures being used to deplete contaminating tumor cells from, for example, an autologous marrow or stem cell suspension. After malignant cell depletion, the treated autologous bone marrow cells (or peripheral blood-derived stem cells) are infused back into the patient who has, in the meanwhile, received appropriate surgical, radiation, immuno- and/or chemotherapy.

In the case of an autologous bone marrow transplantation, the method for removing contaminating cancerous cells from the marrow cell suspension is straightforward, and comprises the steps of (i) collecting an appropriate amount of bone marrow (preferably about 1500 cc from multiple points in the pelvic iliac crest, although as little as 500 cc and as much as 2000 cc can be used) from the individual who has the cancer, and isolating the nucleated cells from the bone marrow sample; (ii) contacting the nucleated bone marrow cells ex vivo (in culture) with a cytotoxically-effective amount of an antisense synthetic oligonucleotide which has a base sequence complementary to the duplex DNA of a target gene (such as, for example, the gene encoding p53) present in the cells of the cancer (this incubation takes from about 12 hours to about 7 days); and (iii) thereafter infusing the treated bone marrow cells back into the individual patient who donated the marrow.

Thus, one method for removing cancerous cells from bone marrow cells obtained from an individual who has cancer involves the steps of:

a) collecting bone marrow cells from the having a cancer;

b) contacting the bone marrow cells ex vivo with a cytotoxically effective amount of at least one synthetic oligonucleotide, which has a base sequence complementary to the duplex DNA of a cancer-related target gene also present in the cells of the cancer;

c) thereafter infusing the treated autologous bone marrow cells back into the individual at a clinically appropriate time.

In a particular embodiment of the present invention, the synthetic oligonucleotide used in treating the bone marrow cells is anti-p53.

This form of intensive therapy can be further improved by the additional step of administering systemically to the individual, after the bone marrow transplant has engrafted, a therapeutic preparation of this invention containing anti-p53 antisense synthetic oligonucleotide, administered in an amount sufficient to kill or inhibit the growth of the few p53-positive cancerous cells which may remain in the individual.

The anti-p53 antisense synthetic oligonucleotides of the present invention can be of significant clinical utility when administered systemically to individuals who have p53-positive cancers, concomitant with or following primary tumor ablation with surgery, radiation and/or chemotherapy. Additional therapeutic gains can be obtained by systematic administration of at least one anti-p53 antisense synthetic oligonucleotide to recipients of autologous bone marrow cell suspensions, after the bone marrow, itself purged of contaminating p53-positive cancer cells by treatment with anti-p53 synthetic oligonucleotide, has engrafted in the individual.

For effective therapeutic utilization of the novel concepts of the present invention, the anti-p53 antisense synthetic oligonucleotides are administered in vivo as a systemic therapy, and they can also be administered in vitro, as a procedure for eliminating contaminating p53-positive tumor cells from a suspension of autologous peripheral blood stem cells or autologous bone marrow cells. Depending on the intended utilization, the physical form of the therapeutic preparation may vary, as discussed more fully hereinafter.

For an "antisense" synthetic oligonucleotide to be useful as a therapeutic agent following systemic administration, it must survive in solution long enough to reach its designated target gene in the body and block the activity of that target gene. To survive in vivo long enough to be effective therapeutically, the synthetic oligonucleotide must be resistant to nucleases.

The "normal" structure of a synthetic oligonucleotide is a defined sequence of synthetic monomers bases built upon a sugar-phosphate backbone containing phosphodiester linkages. There is substantial evidence that these phosphodiester linkages are highly susceptible to rapid degradation by a variety of nucleases found in abundance in tissues and cellular fluids. However, attachment of the modified monomeric structures of the present invention to a phosphodiester backbone results in nuclease resistance. Synthetic oligonucleotides, therefore, do not require a phosphorothioate backbone in order to have nuclease resistance.

Known nuclease-resistant backbone linkage structures can also be employed in the synthetic oligonucleotides of this invention. A number of such linkage structures are known in the art to be nuclease resistant (for example, see the discussion of nuclease-resistant linkages in Stein et al., Nucleic Acids Research 16: 3209-3221, 1988). One such linkage is the phosphorothioate linkage. Phosphorothioates are compounds well known in the art, in which one of the non-bridging oxygen atoms in the phosphate portion of a nucleotide is replaced by sulfur. The use of synthetic oligonucleotide analogs which contain a backbone of phosphorotioate linkages is based on the known resistance of this interbase linkage to degradation by nucleases of many types when used to link the natural nucleotide bases found in DNA or RNA. Since phosphorothioates also have the same number of charges as normal phosphodiester-linked oligomers, they have good aqueous solubility.

The conventional nuclease-resistant phosphorothioate backbone linkage does not diminish the potential for sequence specific recognition by the synthetic oligonucleotide analog for its target gene. Furthermore, it is anticipated that, because of the "abnormal" quinoline and quinazoline bases and the C-glycoside linkage, the synthetic oligonucleotide would be more stable than DNA.

In addition to the preferred phosphorothioate linkage, the "antisense" synthetic oligonucleotides selected for practice of the present invention may have nuclease-resistant ethyl- or methylphosphonate linkages between the synthetic bases. Synthetic oligonucleotide analogs with these types of linkages may be less efficient at hybridization with a complementary DNA sequence than are the corresponding analogs which incorporate phorphorothioate linkages. On the other hand, synthetic oligonucleotides having a methylphosphonate backbone are more lipophilic than are the other analogs, and this may prove advantageous in certain circumstances.

To those skilled in the art, it is known that nuclease-resistant backbone linkages other than those mentioned above are readily available for incorporation into all or part of a newly-synthesized synthetic oligonucleotide. Furthermore, it is also known that other nuclease-resisting linkages are continually being developed. It is the intent of the present invention to include within its scope any "antisense" synthetic oligonucleotide used alone or in combination with other therapies, and which contains such nuclease-resistant backbone linkages.

For systemic administration to a mammalian host, the therapeutic "antisense" synthetic oligonucleotides of the present invention can be formulated into a variety of pharmaceutical compositions, depending upon the protocol to be used for systemic administration. In general, the pharmaceutical compositions employ a therapeutically effective amount of the synthetic oligonucleotide in a dosage and form sufficient to carry out the purpose of the formulation without causing unacceptable toxicity for the patient, i.e., a "pharmaceutically acceptable and effective amount" of the synthetic oligonucleotide. The therapeutic amount which represents an optimal therapeutically-effective dose for treatment of a particular clinical problem can be determined empirically by the chemotherapist. In general it will be the minimal dose which is sufficient to achieve an effective blood concentration of synthetic oligonucleotide and, generally, will fall within the range of from about 0.1 to about 200 micromolar.

The "antisense" synthetic oligonucleotide compounds of the present invention (also referred to hereinafter as the "active ingredients" or "active compounds"), in whatever analog prepared, are administered in a variety of dosage forms. In addition to the active ingredient, any of a number of pharmaceutically-acceptable excipients which facilitate formulation of the active ingredient into suitable dosage form can be used. In a preferred embodiment, the preparations are designed for parenteral administration. However, pharmaceutical compositions designed for oral administration in such forms as tablets, capsules, and dragees, or for rectal administration in the form of suppositories, are also considered to fall within the scope of the present invention.

Appropriate formulations of a therapeutic synthetic oligonucleotide for parenteral administration include aqueous solutions of the active compound prepared in a water-soluble or water-dispersible form. Alternatively, the active compounds are administered as suspensions in appropriate oily injection carriers, i.e., in suitable lipophilic carriers, such as fatty oils (sesame oil being an example), or synthetic fatty acid esters (ethyl oleate or triglycerides being examples). Pharmaceutical formulations prepared for aqueous injection may contain substances which increase the viscosity of the suspension such as, for example, sodium carboxymethyl cellulose, sorbitol, and/or dextran.

The therapeutic "antisense" synthetic oligonucleotides of the present invention may also be administered encapsulated in liposomes. In such pharmaceutical preparations, the "antisense" synthetic oligonucleotides are contained in corpuscles which consist of concentric aqueous layers interspersed between hydrophobic lipidic layers. The synthetic oligonucleotides, depending upon their solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as a diacetylphosphate, stearylamine, or phosphatidic acid, and/or other materials of a hydrophobic nature which are generally well known in the art.

Purging bone marrow suspensions of contaminating tumor cells is presently accomplished either by in vitro incubation of the transplanted marrow cells with potent anti-cancer chemotherapeutic agents, or by contacting the bone marrow cells with immunotherapeutic agents which recognize certain structures unique to the surface membrane of tumor cells.

A major difficulty with immunotherapy is that many tumor cells fail to express the tumor-associated membrane structure, and thereby go unrecognized by the immunotherapeutic agent. On other tumor cells, the immunotherapeutic agent binds to its target but fails to kill the cell. With regard to chemotherapeutic agents, most of the agents are highly toxic and must be used at relatively high dose in order to maximize tumor cell kill. However, this can lead to death of a large number of normal marrow cells and, in some instances, to graft failure. What is needed, therefore, is a bone marrow purging agent which selectively attacks tumor cells and leaves the normal marrow cells intact. The present invention provides such a novel agent for use with cancers of a variety of types. Exemplary are those cancers which are p53-positive cancers.

Thus, in another embodiment of the present invention, anti-p53 antisense synthetic oligonucleotides are used to remove p53-positive cancer cells obtained from the afflicted individual. In this latter technique, bone marrow cells are obtained from an individual who has a p53-positive cancer, using standard procedures, which include aspiration from the pelvic iliac crest of a donor, as described, for example, in U.S. Pat. Nos. 4,481,946 and 4,486,188. The patient from whom the bone marrow has been taken is then treated with radiation or chemotherapy to destroy the p53-positive cancer cells which are in one or more organs of the body. Because this intensive therapy also destroys sensitive stem cells required for reestablishment and regrowth of such vital systems as the hematopoietic system, the treated patient must be replenished with healthy autologous bone marrow cells. Clearly, it is to the long-term advantage of the patient if the bone marrow cells returned to the patient are entirely free of cancer cells. These and other potential concerns are discussed in detail in: Autologous Bone Marrow Transplantation: Proceedings of the Third International Symposium, K. Dicke (Editor), The University of Texas M. D. Anderson Hospital and Tumor Institute at Houston, 1987.

The sample of autologous bone marrow cells is then immediately treated with the anti-p53 synthetic oligonucleotide, as discussed below, and reinfused into the donor as soon as is appropriate. In such a treatment, the autologous bone marrow is purged of contaminating p53-positive cancer cells by exposure ex vivo to a cytotoxically-effective amount of an anti-p53 antisense synthetic oligonucleotide which has a base sequence complementary to that of a p53 target gene present in the cells of the p53-positive cancer.

The time of exposure required to obtain complete elimination of the targeted cells in the bone marrow specimen varies depending on tumor cell target, and must be determined empirically. However, exposure times vary from 1 hour to 4 days or longer. Following exposure to the therapeutic anti-p53 synthetic oligonucleotide preparation, the autologous bone marrow purged of all p53 positive malignant cells is transplanted back into the donor.

Alternatively, if the opportunity or need to use the synthetic oligonucleotide-treated marrow sample is not immediate, the purged bone marrow cells can be frozen and stored until needed. Procedures for preparing and storing bone marrow samples frozen in a viable state are discussed in detail in U.S. Pat. Nos. 4,107,937 and 4,117,881.

The circulating peripheral blood contains a substantial number of mononuclear cells which have the potential to regenerate the complete function of the bone marrow compartment of a host organism, such as a human. These peripheral "stem" cells can be isolated, concentrated, and reintroduced via injection into the peripheral circulation as a "stem cell transplant."

Autologous peripheral blood stem cell transplantation has been found important in facilitating recovery of functional bone marrow after high-dose therapy for a variety of malignant diseases. Autologous peripheral blood stem cell transplantation offers certain advantages to autologous bone marrow transplantation, since the general anesthesia used during bone marrow harvesting can be avoided, the collections of peripheral stem cells can be made in an outpatient setting, and the risk of contamination of the transplanted product with malignant cells appears to be less.

Methods for purging the peripheral stem cell suspension of contaminating tumor cells are very similar, if not identical, to the procedures outlined above for purging bone marrow cells with anti-p53 antisense synthetic oligonucleotides.

It is difficult to determine, prior to a patient's receiving the autologous bone marrow or peripheral stem cell transplant, whether a series of radiotherapy or chemotherapy treatments has completely rid that patient of all p53-positive malignant cells. Therefore, another embodiment of the present invention is to provide a course of systemically-administered antisense oligotherapy as an adjunct therapy to the individual who received the transplant of autologous bone marrow cells or peripheral stem cells.

Of course, in order for the tumor cell targets to be effectively inhibited by the selected antisense synthetic oligonucleotides, the cells must be exposed to the synthetic oligonucleotides under conditions that facilitate their uptake by the malignant cells. This may be accomplished by a number of procedures, including, for example, simple incubation of the cells with the synthetic oligonucleotides in a suitable nutrient medium for a period of time suitable to achieve selective inhibition of the malignant cells. According to the present invention, incubation of bone marrow cells with selected synthetic oligonucleotides (anti-p53 synthetic oligonucleotide, for example) inhibits proliferation of cells after about 8 hours exposure (and possibly sooner). Incubation for at least about 7-10 days kills fresh malignant cells (leukemic blasts, for example) but has no significant effect on fresh cells from normal bone marrow. Accordingly, a preferred procedure for practice of the invention involves placing bone marrow cells into culture, for example, as described by Meagher et al. (Blood 72: 273, 1988) or U.S. Pat. No. 4,721,096, and then incubating with an optimal concentration of the selected antisense synthetic oligonucleotide.

The concentration of synthetic oligonucleotide to be used may vary, depending upon a number of factors, including the type of cancerous cells present in the marrow, the type, and specificity of the particular antisense synthetic oligonucleotide(s) selected, and the relative toxicity of the synthetic oligonucleotide for malignant and normal bone marrow cells. Although it is expected that, according to the present invention, there is significant inhibition of tumor cell DNA synthesis at synthetic oligonucleotide concentrations as low as 30 micromolar, optimal inhibition is expected to be observed at concentrations of at least 60 micromolar. With the aid of the techniques set forth in the present disclosure, those of skill in the art should be able to determine the optimal concentration to be used in a given case.

After the marrow cells have been exposed to the synthetic oligonucleotide and, in some cases, cultured as described above, they are then infused into the transplant recipient to restore hemopoiesis.

The synthetic oligonucleotides of the invention may also be used as sequence specific sentinels that can be used to detect and/or sort cells that differ in DNA sequence. For example, X and Y chromosome containing sperm cells can be detected and/or sorted. Additionally, cells which have been infected with a virus or other foreign agent can be detected and/or sorted. Indeed, the synthetic oligonucleotides of the invention can be directed to a target gene present only in the cell type desired. The synthetic oligonucleotide can then be detectably labeled and the detectably-labeled synthetic oligonucleotide introduced to the cells. Labeled cells can then be detected and/or sorted by methods known in the art.

DEFINITIONS

The following definitions are provided to facilitate an understanding of the present invention:

As used herein, an "oligonucleotide" or "oligomer" is a polymeric chain of at least two chemical subunits, each subunit comprising a nucleotide base moiety, a sugar moiety, and a linking moiety that joins the subunits. "Natural" nucleotide base moieties are guanine (G), adenine (A), cytosine (C), thymine (T) and uracil (U). Preferably, the synthetic oligonucleotides of the invention comprise modified bases which allow triplex formation. Oligonucleotides may optionally include analogs of any of the sugar moieties and the backbone constituents.

As used herein, the term "electron withdrawing group" refers to an atom or substituent that has a relatively high electronegativity, or an ability to acquire electrons from other atoms or groups. An "electron withdrawing group" is capable of withdrawing electrons relative to that of hydrogen if the hydrogen atom occupied the same position on the molecule. The term "electron withdrawing group" is well understood by one skilled in the art and is discussed, for example, in Advanced Organic Chemistry by J. March, John Wiley & Sons, New York, N.Y., (1985). Electron withdrawing groups include, but are not limited to, halo (e.g., fluorine, chlorine, bromine, iodine), nitro, carboxy, cyano, aryl (optionally substituted), heteroaryl, (optionally substituted), $-OC(A)_3$, $-C(A)_3$, $-C(A)_2-O-C(A')_3$, $-(CO)-Q$, $-SO_2-C(A)_3$, $-SO_2$-aryl, $-C(NQ)Q$, $-CH=C(Q)_2$, and $-C\equiv C\text{-}Q$; in which each A and A' is independently H, halo, $-CN$, $-NO_2$, $-OH$, or $C_{1\text{-}4}$ alkyl optionally substituted with 1-3 halo, $-OH$, $NO_2$; and Q is selected from the group consisting of H, $-OH$, alkyl optionally substituted with 1-3 halo, $-OH$, $-O$-alkyl, and $-O$-cycloalkyl. Preferred electron withdrawing groups include fluorine, chlorine, nitro, and cyano.

The terms "halogen," "halo," and "halide" refer to chlorine, bromine, fluorine or iodine.

The term "alkyl," as employed herein, includes both straight and branched chain hydrocarbons containing 1 to 10 carbons, preferably 1 to 8 carbons, more preferably 1 to 4 carbons, in the normal chain. Examples of suitable alkyl groups include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, the various branched chain isomers thereof, and the like. Each alkyl group may optionally be substituted with 1 to 4 substituents which include, for example, halo, —OH, —O— alkyl, and —O-cycloalkyl.

The term "cycloalkyl," as employed herein includes saturated or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), preferably 3 to 10 carbons forming the ring(s), and may optionally be fused to 1 or 2 aromatic rings as described for aryl, below. Unsaturated cycloalkyl groups may contain one or two double bonds, or one triple bond. Cycloalkyl groups include, without limitation, cyclopropyl, cyclobutyl, cyclopentyl, cyclohexyl, cycloheptyl, cyclooctyl, cyclodecyl and cyclododecyl, cyclopentenyl, cyclohexenyl, cycloheptenyl, cyclooctenyl, cyclohexadienyl, and cycloheptadienyl. Each cycloalkyl group may be optionally substituted with 1 to 4 substituents such as halogen, alkyl, alkoxy, hydroxy, aryl, aryloxy, aralkyl, cycloalkyl, alkylamido, alkanoylamino, oxo, acyl, arylcarbonylamino, amino, substituted amino, nitro, cyano, thiol and/or alkylthio.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino.

"Heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

The term "leaving group" refers to an atom or substituent capable of being displaced by a nucleophile. Exemplary leaving groups include, without limitation, halogen (e.g., chloro, fluoro, bromo, iodo), alkylsulfonyl, substituted alkylsulfonyl, arylsulfonyl, substituted arylsulfonyl, hetercyclcosulfonyl, and trichloroacetimidate, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups.

The term "protecting group" refers to an atom or a subsituent that reduces or prevents the reactivity of a reactive group in a molecule. Examples of protecting groups can be found in T. W. Greene and P. G. Futs, Protective Groups in Organic Chemistry, (Wiley, 2nd ed. 1999); Beaucage, et al. (1992) Tetrahedron, 12:2223; and Harrison and Harrison et al., Compendium of Synthetic Organic Methods, Vols. 1-8 (John Wiley and Sons. 1971-1996). Exemplary hydroxyl protecting groups include, without limitation, t-butyldimethylsilyl (TBDMS), t-butyldiphenylsilyl (TBDPS), dimethoxytrityl (DMT), and monomethoxytrityl (MMT).

As used herein, the term "phosphoramidite form" refers to a nucleotide wherein the 5' primary hydroxyl of the deoxyribose sugar is protected (e.g., dimethyoxytrityl (DMT) or monomethoxytrityl (MMT) protected) and the 3' secondary hydroxyl of the deoxyribose sugar is derivatized with the highly reactive phosphoramidite group, wherein the phosphate oxygen is usually masked by, for example, β-cyanoethyl or methyl protecting groups and diisopropylamine or dimethylamine protecting groups (see generally, Ausubel et al., eds. Current Protocols in Molecular Biology, John Wiley and Sons, Inc., (1998)).

As used herein, the term "oligonucleotide analog backbone" refers to any oligomeric analog of the natural sugar phosphate backbone of nucleic acid molecules. Oligonucleotide analog backbones include, for example, phosphate modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl substitutions (see, e.g., Hunziker and Leumann (1995) Nucleic Acid Analogues: Synthesis and Properties, in Modern Synthetic Methods, VCH, 331-417; Mesmaeker et al. (1994) Novel Backbone Replacements for Oligonucleotides, in Carbohydrate Modifications in Antisense Research, ACS, 24-39). Oligonucleotide analog backbones may also comprise modified sugars (see, e.g., U.S. Patent Application Publication No. 2005/0118605). Oligonucleotide analog backbones also include oligonucleotide mimetics such as, without limitation, peptide nucleic acids (PNA), morpholino nucleic acids, cyclohexenyl nucleic acids, anhydrohexitol nucleic acids, and locked nucleic acids (LNA) (see, e.g., U.S. Patent Application Publication No. 2005/0118605). The term "unit of an oligonucleotide analog backbone" refers to the individual monomers of the oligonucleotide analog backbone.

The following examples describe illustrative methods of practicing the instant invention and are not intended to limit the scope of the invention in any way. All reagents employed in Example 1 were of the highest grade commercially available and used without any purification. NMR studies were performed on a Varian ANOVA 500 MHz instrument.

EXAMPLE 1

2-amino-6-fluoro-4-(2'-deoxy-β-D-ribofuranosyl)-quinoline

A method of synthesizing the monomer antiAT-F, which exhibits superior results in the solid phase synthesis of oligonucleotides as compared to antiAT, is provided herein.

Synthesis of 2-Amino-6-fluoro-4-hydroxyquinoline (1). 4-Fluoroanilinium toluene-p-sulphonate (76 g) is heated at 260° C. for 5 minutes under $N_2$ and ethyl cyanoacetate (30 g) was added dropwise through an air-condenser within 5 minutes. The temperature of the reaction was allowed to drop to 220-250° C. After 90 minutes of heating, the orange slurry was cooled, $CHCl_3$ (100 mL) was added, and the resulting mixture refluxed overnight to dissolve the solid. This solution was vigorously mixed with $H_2O$ (100 mL), EtOH (40 mL), and saturated $Na_2CO_3$ solution (100 mL). The resulting slurry was filtered, and the product, a pale-yellow solid, dried in vacuo over $P_2O_5$ (7.4 g, 15% yield): $^1H$ NMR (DMSO-$d_6$) δ 5.26 (bs, 1 H), 6.22 (s, 2 H, $NH_2$), 7.32 (m, 2 H), 7.55 (d, 1 H, J=8.5), 10.79 (bs, 1 H, OH); HRMS-FAB ($M^+$) calculated for 178.0542, found 178.0545.

Synthesis of 2-amino-4-bromo-6-fluoroquinoline (2). 1 (7.2 g) was heated with $POBr_3$ (22.0 g) in $PBr_3$ (20 ml) at 140-160° C. under $N_2$ for 19 hours. The reaction was cooled, carefully basified with 2 M NaOH (250 mL) and thrice extracted with $CHCl_3$ (30 mL). The organic layer was concentrated, and the residue purified by silica gel chromatography using $CHCl_3$/acetone/$Et_3N$ (75:25:1) to afford the product that was re-crystallized from benzene/$CH_2Cl_2$/hexane to furnish off-white crystals (5.5 g, 57% yield): $^1H$ NMR ($CDCl_3$) δ 4.70 (bs, 2 H, $NH_2$), 7.10 (s, 1 H), 7.37 (m, 1 H), 7.66 (m, 2 H); HRMS-FAB ($M^+$) calculated for 239.9698, found 239.9707.

Synthesis of 4-[β-D-glyceropentofuran-3'-ulos-1'-yl]-2-amino-6-fluoroquinoline (3). 1,4-Anhydro-3-O—(tert-butyldiphenylsilyl)-2-deoxy-D-erythro-pent-1-enitol (2.13 g) (Farr and Davies, Carbohydr. Chem. (1990) 9:653-660) and 2 (1.21 g) were dissolved in dioxane (100 mL) under $N_2$. Then bis(dibenzlideneacetone)Pd(0) (0.81 g) and (t-Bu)$_3$P (0.71 mL) were added to the reaction. After the reaction had been purged with $N_2$ for 15 minutes, dicyclohexylmethylamine (1.35 mL) was added and the mixture refluxed under $N_2$ for 20 hours. The reaction was cooled, filtered and the filtrate concentrated in vacuo. The residue was subject to silica gel chromatography with $CH_2Cl_2$—$CH_2Cl_2$/MeOH (gradient from 100 to 95%) to give the desired nucleoside and the quinoline-quinoline dimer side-product in a ratio 2:1 (total 1.95 g). This mixture was dissolved in THF (40 mL) containing HOAc (0.4 mL), $Bu_4NF$ (5 mL, 1 M in THF) and stirred at 0° C. for 50 minutes. Then $NH_4OH$ (2 mL) was added and the solution concentrated in vacuo. The residue is subjected to silica gel column chromatography with $CH_2Cl_2$—$CH_2Cl_2$/MeOH (gradient from 100% to 91%) to give the desired desilylated product (0.46 g, 33% overall yield): $^1H$ NMR ($CDCl_3$) δ 2.23 (dd, 1 H, J=13.0, 11.0, C2'-H), 3.08 (dd, 1 H, J=13.0, 11.0, C2''-H), 4.01-4.17 (m, 2 H, C5'-H, C5''-H), 4.20 (m, 1 H, C4'-H), 5.63 (dd, 1 H, J=7.5, 5.5, C1'-H), 6.15- (bs, 2H, $NH_2$), 7.25 (s, 1 H, overlapped with solvent signal), 7.28 (m, 2 H), 7.67 (m, 1 H); HRMS-FAB ($M^+$) calculated for 276.0910, found 276.0914.

Synthesis of 2-amino-6-fluoro-4-(2'-deoxy-β-D-ribofuranosyl)-quinoline (antiAT-F) (4). 3 (1.1 g) was dissolved in AcOH and $CH_3CN$ (100 mL, 1:1) and stirred under $N_2$ at −23° C. in a solid $CO_2$/$CCl_4$ bath. $NaHB(OAc)_3$ (1.4 g) was added to the cooled solution and the mixture stirred at −23° C. for 30 minutes. The reaction was concentrated and the residue chromatographed on silica gel using $CH_2Cl_2$/MeOH (gradient from 10:1 to 2:1). The crude product was obtained as a pale yellow powder, which was crystallized from $Et_2O$/EtOH to yield an off-white powder (0.77 g, 70% yield): m.p. 69-70° C.; $^1H$ NMR (DMSO-$d_6$) δ 1.73-1.78 (m, 1 H, C2'-H), 2.33-2.37 (m, 1 H, C2''-H), 3.45 (dd, 1H, J=11.5, 6.0, C5'-H), 3.56 (dd, 1 H, J=11.5, 6.0, C5''-H), 3.85-3.88 (m, 1 H, C4'-H), 4.18 (m, 1 H, C3'-H), 4.77 (bs, 1 H, OH3'), 5.15 (bs, 1 H, OH5'), 5.45 (dd, 1 H, J=10.0, 5.5, C1'-H), 6.37 (s, 2 H, $NH_2$), 6.96 (s, 1 H), 7.32-7.36 (m, 1 H), 7.41-7.49 (m, 2 H); $^{19}F$ NMR (DMSO-$d_6$): δ −90.26 (one single peak with multiple splits, referenced by TFA in $H_2O$); HRMS-FAB ($M+H^+$) calculated for 278.1067, found 278.1070.

Synthesis of N2-isobutyryl-4-[2'-deoxy-β-D-threo-pentofuranosyl]-2-amino-6-fluoroquinoline (5). 4 (0.88 g) in dry pyridine (50 mL) was cooled in an ice bath and treated with TMS-Cl (4.8 mL) under $N_2$. The reaction was stirred at 0° C. for 30 minutes, then isobutyric anhydride (2.62 mL) was added and the reaction stirred for an additional 2 hours at room temperature under $N_2$. The reaction was then cooled in an ice bath and cold $H_2O$ (6.25 mL) added. After 15 minutes, conc. $NH_4OH$ (6.25 mL) was added to give a solution approximately 2 M in $NH_3$. This mixture was stirred for another 30 minutes in ice bath then concentrated under reduced pressure to afford an oil that was purified on silica gel with $CH_2Cl_2$/MeOH (10:1) to furnish the desired product as a pale yellow solid (0.53 g, 47% yield) : $^1H$ NMR ($CDCl_3$) δ 1.31 (dd, J=6.0, 0.5, 6 H), 2.13-2.18 (m, 1 H, C2'-H), 2.57-2.64 (m, 2 H, including C2''-H), 3.86 (dd, 1 H, J=17.5, 4.5, C5'-H), 4.01 (dd, 1 H, J=17.5, 4.5, C5''-H), 4.21 (dd, 1 H, J=7.5, 3.5, C4'-H), 4.57 (m, 1 H, C3'-H), 5.77 (dd, 1 H, J=9.0, 8.5, C1l'-H), 7.43 (m, 1 H), 7.53 (m, 1 H), 7.84 (m, 1 H), 8.13 (s, 1 H), 8.68 (s, 1 H); HRMSFAB ($M^+$) calculated for 348.1485, found 348.1492.

Synthesis of N2-isobutyryl-4-[2'-deoxy-β-D-threo-pentofuranosyl-5'-O-(4,4'-dimethoxytrityl)]-2-amino-6-fluoroquinoline (6). 5 (0.4 g) was dissolved in dry pyridine (10 mL) under a $N_2$ atmosphere. Then 4,4'-dimethoxytrityl chloride (0.5 g) and DMAP (10 mg) are added to the solution at room temperature. Another aliquot of trityl chloride was added after 3 hours and the reaction stirred under $N_2$ at room temperature for a total of 6 hours. After concentration, the residue was dissolved in $CHCl_3$ (30 mL), washed thrice with saturated $NaHCO_3$ (30 mL) and thrice with $H_2O$ (30 mL). The solution was concentrated and the residue chromatographed on silica gel with $CH_2Cl_2$/MeOH/$Et_3N$ (100:0:1-100:1:1). The final product was a white solid (0.43 g, 58% yield): $^1H$ NMR ($CDCl_3$) δ 1.28 (dd, J=7.5, 6.5, 6 H), 2.20-2.25 (m, 1 H, C2'-H), 2.46-2.51 (m, 1 H, C2''-H), 2.55-2.61 (m, 1 H), 3.36 (dd, 1 H, J=9.5, 5.5, C5'-H), 3.51 (dd, 1 H, J=9.5, 5.5, C5''-H), 3.79 (s, 6 H), 4.09-4.12 (m, C4'-H), 4.43-4.45 (m, 1 H, C3'-H), 5.65 (dd, 1 H, J=10.0, 6.0, C1'-H), 6.80-6.82 (m, 4 H), 7.18-7.48 (m, 10 H), 7.68 (dd, 1 H, J=9.5, 2.5), 7.83 (dd, 1 H, J=9.5, 5.5), 8.00 (bs, 1 H), 8.61 (s, 1 H); HRMS-FAB ($M+H^+$) calculated for 651.2871, found 651.2862.

Synthesis of N2-Isobutyryl-4-[2'-deoxy-β-D-threo-pentofuranosyl-3'-O-(2-cyanoethoxy)(diisopropylamino) phosphino-5'-O-(4,4'-dimethoxytrityl)]-2-amino-6-fluoroquinoline (7). 6 (0.1 g) dissolved in $CH_2Cl_2$ (10 mL) and cooled in an ice bath under $N_2$ atmosphere was treated with Hunig's base (0.2 mL) followed by 2-cyanoethyl-N,N-diisopropylphosphoramidite (0.09 mL). The reaction was stirred at 0° C. for 10 minutes then at room temperature for 45 minutes. After concentration in vacuo, the residue was purified by column chromatography on silica gel with $CH_2Cl_2$/hexane/$Et_2O$/$Et_3N$ (50:100:150:1). The final product was a white powder (0.11 g, 84% yield): $^1H$ NMR ($CDCl_3$) δ 1.12-1.30 (m, 20 H), 2.18-2.28 (m, 1 H, C2'-H), 2.47-2.67 (m, 3 H, including C2''-H), 3.38-3.42 (m, 2 H, C5'-H, C5''-H), 3.31-3.57 (m, 1 H), 3.60-3.70 (m, 1 H), 3.78 (s, 6 H), 4.31 (bs, 1 H, C4'-H), 4.55 (m, 1 H, C3'-H), 5.65 (dd, 1 H, J=10.5, 5.0, C1'-H), 6.77-6.81 (m, 4 H), 7.16-7.45 (m, 10 H), 7.74 (dd, 1 H, J=10.5, 3.0), 7.83 (dd, 1 H, J=9.5, 5.5), 7.96 (s, 1 H), 8.64 (s, 1 H); HRMS-FAB ($M+H^+$) calculated for 851.3950, found 851.3967.

pKa of antiAT-F (4). To 4 (1.62 mg) dissolved in $H_2O$ was added NaOAc buffer to give solutions (1.24 μM final concentration) with measured pH values of 4.602, 5.462, 5.851, 6.153, 6.608, 6.761, 7.2182, 7.508, and 8.322. Two methods were used to measure the pKa. First, the UV spectra of these solutions were recorded from 200-400 nm. The UV spectra at the different pH's were analyzed by plotting absorbance at 235 nm as a function of pH to calculate the pKa.

Second, the fluorescence emission spectra of these solutions were recorded from 300-600 nm with excitation at 330 nm. The fluorescence spectra at different pH's were analyzed by plotting I (391 nm), I (396 nm), I (402 nm), or the shifts of maximum wavelength, respectively, as a function of pH to calculate the pKa. Both methods gave a calculated pKa of 6.7.

NMR conformational studies. The conformational analysis of antiAT-F (4) was determined by $^1$H NMR on a Varian ANOVA (ANalysis Of VAriance) 500-MHz Spectrometer using NOESY (Nuclear Overhauser Enhancement SpectroscopY) with presaturation field strength γB1 of 50 Hz and a mixing time of 0.4 seconds at 25° C. in 10 mM sodium phosphate buffer (pH 7.0) in D$_2$O containing 50 mM NaCl. For antiAT-F (4), the sample concentration was 14.8 mM, and the relaxation delay was 2.1 seconds.

EXAMPLE 2

Intramolecular Triplex Formation with antiAT-F

The ability of antiAT-F (4) to form a triplex structure with high specificity with A:T base pairs was evaluated by determining the stability of a series of putative intramolecular triplexes using UV-visible spectroscopy. The antiAT-F deoxynucleoside has a $\lambda_{max}$ at 325 nm, which makes it convenient to monitor absorbance changes commonly observed for aromatic systems when they unstack from a triplex or duplex. In addition, by monitoring the $\lambda_{max}$ at 260 nm it is possible to observe the natural nucleobases as the duplex segment melts. It has previously been observed that 2 the extinction coefficient of fluoro-substituted quinolines decreases by approximately 35% as the environment of the heterocycle changes from less polar (95% EtOH) to more polar (10% EtOH) solvent (Miller et al. (1950) J. Am. Chem. Soc., 72:1629-1633). This is the opposite of what is observed for the natural nucleobases; therefore, the temperature-dependent UV-vis of the antiAT-F C-glycoside was determined. There is a clear hypochromicity as the temperature increases and this temperature-dependent decrease in the extinction coefficient is corrected for in analyzing the chromicity changes in the melting experiments using OL-1 and OL-2. In both OL-1 and OL-2 (FIG. 3), an antiAT-F is matched with an A:T base pair, although the directionality for triplex formation is reversed (FIG. 4). In OL-1, which has a $T_M$ of 38° C. at pH 7.0, the triplex presumably anneals into the duplex from its 5' to 3' terminus, while the opposite is the case for OL-2 (FIG. 3). Both OL-1 and OL-2 show a two-state transition between triplex and random coil based upon the UV-vis spectra at both 260 and 325 nm (FIG. 4). The $T_M$ and hyperchromicity increase with increasing salt concentration at both wavelengths. There is no significant difference in the stabilities of triplexes OL-1 and -2 from analysis of the melting curves (FIG. 4), although at pH 7.0 OL-2 shows more hyperchromicity, as well as a more cooperative melting curve. In OL-2 the third strand anneals 3'→5' relative to the duplex, whereas the reverse direction (5'→3') occurs for OL-1. Previously, it was observed in intramolecular triplexes that antiGC runs have a very modest preference to bind 5'→3'; however, antiCG shows a very strong preference for the 5'→3' annealing orientation. This same 5'→3' preference for nucleation for pyrimidine triple helix-forming oligonucleotides has been reported for intermolecular triplexes (Alberti et al. (2002) Nucl. Acids Res., 30:5407-5415). It has been previously reported that an intramolecular triplex composed of T:A base pairs, 5'-d(antiTA$_6$-C$_5$-T$_6$-C$_5$-A$_6$) has a $T_M$ of 25° C. (Li et al. (2003) J. Am. Chem. Soc., 125, 2084-2093). This is substantially lower than reported here for OL-2, which has the same folding orientation and number of triplets.

Because specific recognition of an A:T pair requires antiAT-F to be neutral at physiological pH, triplex formation was studied as a function of pH over the range of 6.0 to 8.0. There is a clear pH dependency in terms of $T_M$ and hyperchromicity at 325 nm for both OL-1 and OL-2. The stability and hyperchromicity for the former are higher at the more basic 8.0 pH where approximately 2% of antiAT-F is protonated. OL-2 appears to be less sensitive to pH as there is little difference in the melting curves at pH 7.0 or 8.0. However, at pH 6.0 no triplex is formed.

Another approach to determine the specificity of antiAT-F was to replace a single A:T in OL-2 with either a G:C (OL-3) or T:A (OL-4) base pair. These changes should introduce mismatches between the antiAT-F segment and the duplex causing a reduction in triplex stability. The results corroborate this expectation (FIG. 4): both OL-3 and OLO-4 show a strong inhibition of the temperature-dependent hyperchromicity when monitored at 325 nm. This suggests that at neutral pH, antiAT-F only binds stably to A:T. Moreover, the $T_M$ studies at pH 6 and 8 (FIG. 4) demonstrate that only at neutral pH or above is there evidence for a triplex structure with antiTA-F (OL-1 and OL-2). This is consistent with the protonation of antiAT-F at pH 6.0 which would convert antiAT-F to antiAT-F+ and from an A:T to a G:C binder (FIG. 5). In a final set of experiment to evaluate the fidelity of antiAT-F for A:T pairs at neutral pH, OL-5 was synthesized. In this construct the Watson-Crick duplex is all G:C's and if antiAT-F could bind to G:C pairs at neutral pH a triplex would be observed.

In summary, a synthetic route to a C-nucleoside that specifically binds to A:T base pairs via a triplex structure has been developed. The antiAT-F glycoside provides the four necessary monomers needed to form a stable triplex at any sequence of native DNA.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of the formula:

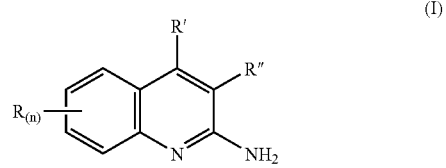

(I)

wherein R is selected from the group consisting of fluorine, chlorine, nitro, and cyano, n is an integer from 1-4, each said R substituent being the same or different when the benzene ring of the compound of Formula (I) is polysubstituted, R' is a selected from the group consisting of ribose, deoxyribose, optionally comprising at least one phosphate, the phosphoramidite form of such compound, and a unit of an oligonucleotide analog backbone; and R" is H or R and wherein the amino substituent of said compound is optionally protected by a protecting group, said protecting group being selected from the group consisting of acyl and aroyl protecting groups.

2. A compound of the formula:

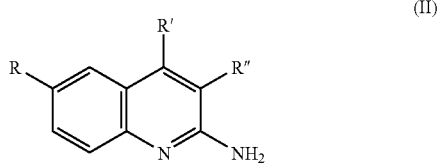

wherein R is selected from the group consisting of fluorine, chlorine, nitro, and cyano, R' is a selected from the group consisting of ribose and deoxyribose, optionally comprising at least one phosphate, the phosphoramidite form of such compound, and a unit of an oligonucleotide analog backbone; and R" is H or R and wherein the amino substituent of said compound is optionally protected by a protecting group, said protecting group being selected from the group consisting of acyl and aroyl protecting groups.

3. The compound 2-amino-6-fluoro-4(2'-deoxy-β-D-ribofuranosyl) quinoline, according to claim 2.

4. The compound according to claim 1, having a protecting group on the amino substituent group thereof.

5. The compound according to claim 2, having a protecting group on the amino substituent group thereof.

6. The compound according to claim 2, having a protecting group on the amino substituent group thereof.

7. The compound according to claim 6, wherein said protecting group is selected from the group consisting of acyl and aroyl protecting groups.

8. The compound according to claim 3, having an isobutyroyl protecting group on the amino substituent thereof.

9. The compound according to claim 1 in the form of a phosphoramidite.

10. The compound according to claim 2 in the form of a phosphoramidite.

11. An oligonucleotide comprising a compound of claim 1.

12. An oligonucleotide comprising a compound of claim 3.

13. An oligomer comprising a compound of claim 1.

14. An oligomer comprising a compound of claim 3.

15. An oligonucleotide comprising a compound of claim 2.

16. An oligomer comprising a compound of claim 2.

* * * * *